(12) United States Patent
Heindl et al.

(10) Patent No.: US 7,541,448 B2
(45) Date of Patent: Jun. 2, 2009

(54) OLIGONUCLEOTIDES CONTAINING MOLECULAR RODS

(75) Inventors: Dieter Heindl, Paehl (DE); Astrid Reiser, Antdorf (DE); Karim Tabiti, Poecking (DE); Martina Junius, Tutzing (DE); Alexander Hauber, Wielenbach (DE)

(73) Assignee: Roche Diagnostis Operations, Inc., Indianapolis, IN (US)

( * ) Notice: Subject to any disclaimer, the term of this patent is extended or adjusted under 35 U.S.C. 154(b) by 349 days.

(21) Appl. No.: 11/001,785

(22) Filed: Dec. 2, 2004

(65) Prior Publication Data

US 2005/0142598 A1 Jun. 30, 2005

(30) Foreign Application Priority Data

Dec. 2, 2003 (EP) .................... 03027753

(51) Int. Cl.
*C07H 21/02* (2006.01)
*C07H 21/04* (2006.01)
*C07H 19/04* (2006.01)
*G01N 33/53* (2006.01)
*C12Q 1/68* (2006.01)

(52) U.S. Cl. ............ 536/23.1; 536/24.3; 536/25.3; 536/26.6; 435/6; 436/808

(58) Field of Classification Search ......... 536/23.1, 536/24.3, 25.3, 26.6; 435/6; 436/808
See application file for complete search history.

(56) References Cited

U.S. PATENT DOCUMENTS 5,118,801 A 6/1992 Lizardi et al.
5,141,837 A 8/1992 Nguyen et al.
5,210,015 A 5/1993 Gelfand et al.
5,290,925 A 3/1994 Fino
5,487,972 A 1/1996 Gelfand et al.
5,538,848 A 7/1996 Livak et al.
5,679,554 A * 10/1997 Goodchild et al. ....... 435/91.31
5,770,715 A 6/1998 Sugiyama et al.
5,804,375 A 9/1998 Gelfand et al.
5,932,711 A 8/1999 Boles et al.
6,174,670 B1 1/2001 Wittwer et al.
2003/0092901 A1 5/2003 Farooqui et al.

(Continued)

FOREIGN PATENT DOCUMENTS

WO WO 97/46707 12/1997

(Continued)

OTHER PUBLICATIONS

Bernard, Philip et al., "Integrated Amplification and Detection of the C6777T Point Mutation in the Methylenetetrahydrofolate Reductase Gene by Fluorescence Resonance Energy Transfer and Probe Melting Curves," Analytical Biochemistry 255, 101-107 (1998) Article No. AB972427.

(Continued)

*Primary Examiner*—Jezia Riley
(74) *Attorney, Agent, or Firm*—Marilyn L. Amick; Roche Diagnostics Operations, Inc.

(57) ABSTRACT

The invention is directed to an oligonucleotide comprising a molecular rod, wherein preferentially the molecular rod covalently connects the 3' end of a first nucleotide residue with the 5' end of a second nucleotide residue. Such oligonucleotides are highly advantageous for real time PCR melting curve analysis.

17 Claims, 7 Drawing Sheets

U.S. PATENT DOCUMENTS

| | | |
|---|---|---|
| 2003/0143616 A1 | 7/2003 | Kuimelis et al. |
| 2003/0190660 A1 | 10/2003 | Lowe et al. |
| 2004/0034043 A1* | 2/2004 | Katzhendler et al. ... 514/263.38 |

FOREIGN PATENT DOCUMENTS

| | | |
|---|---|---|
| WO | WO 97/46712 | 12/1997 |
| WO | WO 97/46714 | 12/1997 |
| WO | WO 03/059881 A2 | 7/2003 |

OTHER PUBLICATIONS

Matthews, Jayne et al., "Analytical Strategies for the Use of DNA Probes," Analytical Biochemistry 169, 1-25(1998).

Schwab, Peter et al., "Molecular Rods. 1. Simple Axial Rods," Chem. Rev. 1999, 99, 1863-1933.

* cited by examiner

———————  homozygous wildtype

- - - - -  heterozygous

—□—  homozygous mutant

— —  negative control

———— homozygous wildtype

- - - - - heterozygous

—□— homozygous mutant

— — negative control homozygous wildtype ——— heterozygous - - - - - homozygous mutant —o— negative control — —

$T_M$

| | perfect match | 57.80°C |
|---|---|---|
| - - - - | additional mismatch | 52.13°C |
| —◦— | phenylene linker | 46.28°C |
| — — | negative control | |

—————— $10^4$ EBV copies

— — negative control

——— $10^4$ EBV copies
— — negative control

SEQUENCE LISTING

```
<160> NUMBER OF SEQ ID NOS: 11

<210> SEQ ID NO 1
<211> LENGTH: 21
<212> TYPE: DNA
<213> ORGANISM: Artificial
<220> FEATURE:
<223> OTHER INFORMATION: prothrombin forward primer

<400> SEQUENCE: 1
ccaatcccgt gaaagaatta t                                        21

<210> SEQ ID NO 2
<211> LENGTH: 20
<212> TYPE: DNA
<213> ORGANISM: Artificial
<220> FEATURE:
<223> OTHER INFORMATION: prothrombin reverse primer

<400> SEQUENCE: 2
aggtggtgga ttcttaagtc                                          20

<210> SEQ ID NO 3
<211> LENGTH: 35
<212> TYPE: DNA
<213> ORGANISM: Artificial
<220> FEATURE:
<223> OTHER INFORMATION: prothrombin probe 1

<400> SEQUENCE: 3
cacttttatt gggaaccata gttttagaaa cacaa                         35

<210> SEQ ID NO 4
<211> LENGTH: 20
<212> TYPE: DNA
<213> ORGANISM: Artificial
<220> FEATURE:
<223> OTHER INFORMATION: prothrombin probe 2

<400> SEQUENCE: 4
gcattgaggc tcgctgagag                                          20

<210> SEQ ID NO 5
<211> LENGTH: 20
<212> TYPE: DNA
<213> ORGANISM: Artificial
<220> FEATURE:
<223> OTHER INFORMATION: prothrombin probe 3

<400> SEQUENCE: 5
gcattgtggc tcgctgagag                                          20
```

<210> SEQ ID NO 6
<211> LENGTH: 20
<212> TYPE: DNA
<213> ORGANISM: Artificial
<220> FEATURE:
<223> OTHER INFORMATION: prothrombin probe 4
<220> FEATURE:
<221> NAME/KEY: misc_feature
<223> OTHER INFORMATION: n in position 7 denotes a phenylene linker
<220> FEATURE:
<221> NAME/KEY: misc_feature
<222> LOCATION: (7)..(7)
<223> OTHER INFORMATION: n is a, c, g, or t

<400> SEQUENCE: 6
gcattgnggc tcgctgagag                                               20

<210> SEQ ID NO 7
<211> LENGTH: 22
<212> TYPE: DNA
<213> ORGANISM: Artificial
<220> FEATURE:
<223> OTHER INFORMATION: EBV forward primer

<400> SEQUENCE: 7
atgaggaacg tgaatctaat ga                                            22

<210> SEQ ID NO 8
<211> LENGTH: 25
<212> TYPE: DNA
<213> ORGANISM: Artificial
<220> FEATURE:
<223> OTHER INFORMATION: EBV reverse primer

<400> SEQUENCE: 8
tacagataga tggcactctt acctt                                         25

<210> SEQ ID NO 9
<211> LENGTH: 26
<212> TYPE: DNA
<213> ORGANISM: Artificial
<220> FEATURE:
<223> OTHER INFORMATION: EBV probe 1

<400> SEQUENCE: 9
gggattgcaa cacgacggga atgacg                                        26

<210> SEQ ID NO 10
<211> LENGTH: 23
<212> TYPE: DNA
<213> ORGANISM: Artificial
<220> FEATURE:
<223> OTHER INFORMATION: EBV probe 2

<400> SEQUENCE: 10
gctccctccc cctccctact ctc                                           23

<210> SEQ ID NO 11
<211> LENGTH: 23
<212> TYPE: DNA
<213> ORGANISM: Artificial
<220> FEATURE:
<223> OTHER INFORMATION: EBV probe 3
<220> FEATURE:
<221> NAME/KEY: misc_feature
<223> OTHER INFORMATION: n in position 15 denotes a phenylene linker
<220> FEATURE:

```
<221> NAME/KEY: misc_feature
<222> LOCATION: (15)..(15)
<223> OTHER INFORMATION: n is a, c, g, or t

<400> SEQUENCE: 11
gctccctccc cctcnctact ctc                                                        23
```

OLIGONUCLEOTIDES CONTAINING MOLECULAR RODS

FIELD OF INVENTION

The present invention relates to the field of chemically modified oligonucleotides. More precisely, the present invention relates to the field of providing chemically modified oligonucleotides which can be used as hybridization probes either in real time PCR or nucleic acid array technology.

BACKGROUND OF THE INVENTION

Amplification of DNA by polymerase chain reaction (PCR) is a technique fundamental to molecular biology. Nucleic acid analysis by PCR requires sample preparation, amplification, and product analysis. Although these steps are usually performed sequentially, amplification and analysis can occur simultaneously. DNA dyes or fluorescent probes can be added to the PCR mixture before amplification and used to analyze PCR products during amplification. Sample analysis occurs concurrently with amplification in the same tube within the same instrument. This combined approach decreases sample handling, saves time, and greatly reduces the risk of product contamination for subsequent reactions, as there is no need to remove the samples from their closed containers for further analysis. The concept of combining amplification with product analysis has become known as "real time" PCR. See, for example, U.S. Pat. No. 6,174,670.

Real Time PCR Detection Formats

In kinetic real time PCR, the formation of PCR products is monitored in each cycle of the PCR. The amplification is usually measured in thermocyclers which have additional devices for measuring fluorescence signals during the amplification reaction.

DNA binding dye formats: Since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double-stranded DNA. Preferably, only those dyes may be used which, like SybrGreenI I, for example, do not affect the efficiency of the PCR reaction.

All other formats known in the art require the design of a fluorescent labeled hybridization probe which only emits fluorescence upon binding to its target nucleic acid.

TAQMAN probes: A single-stranded hybridization probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq polymerase during the subsequent elongation phase. As a result the excited fluorescent component and the quencher are spatially separated from one another and thus a fluorescence emission of the first component can be measured. TAQMAN probe assays are disclosed in detail in U.S. Pat. Nos. 5,210,015 5,538,848, and 5,487,972. TAQMAN hybridization probes and reagent mixtures are disclosed in U.S. Pat. No. 5,804,375.

Molecular beacons: These hybridization probes are also labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801). Molecular beacons can be used for melting curve analysis in order to identify specific alleles or polymorphisms (see below).

FRET hybridization probes: The FRET hybridization probe test format is especially useful for all kinds of homogenous hybridization assays (Matthews, J. A., and Kricka, L. J., Analytical Biochemistry 169 (1988) 1-25. It is characterized by two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected.

When annealed to the target sequence, the hybridization probes must sit very close to each other, in a head to tail arrangement. Usually, the gap between the labeled 3' end of the first probe and the labeled 5' end or the second probe is as small as possible, i.e. 1-5 bases. This allows for a close vicinity of the FRET donor compound and the FRET acceptor compound, which is typically 10-100 Angstroem.

Alternatively to monitoring the increase in fluorescence of the FRET acceptor component, it is also possible to monitor fluorescence decrease of the FRET donor component as a quantitative measurement of hybridization event.

In particular, the FRET hybridization probe format may be used in real time PCR, in order to detect the amplified target DNA. Among all detection formats known in the art of real time PCR, the FRET-hybridization probe format has been proven to be highly sensitive, exact and reliable (WO 97/46707; WO 97/46712; WO 97/46714). Yet, the design of appropriate FRET hybridization probe sequences may sometimes be limited by the special characteristics of the target nucleic acid sequence to be detected.

As an alternative to the usage of two FRET hybridization probes, it is also possible to use a fluorescent-labeled primer and only one labeled oligonucleotide probe (Bernard, P. S., et al., Analytical Biochemistry 255 (1998) 101-107). In this regard, it may be chosen arbitrarily, whether the primer is labeled with the FRET donor or the FRET acceptor compound.

There exist many different pairs of fluorescent dyes known in the art which according to the invention are principally capable of acting together as a FRET donor/FRET acceptor pair. Yet, prior to the present invention, no functional example has been disclosed, characterized in that 4 different FRET pairs have succesfully been used in a multiplex detection assay. Among other reasons, this may be due to lack of appropriate instrumentation and, moreover, due to fact that the functionality of the FRET process of a specific FRET pair is interfered by other fluorescent compounds which are present in the same reaction mixture.

Besides PCR and real time PCR, FRET hybridization probes and molecular beacons are used for melting curve analysis. In such an assay, the target nucleic acid is amplified first in a typical PCR reaction with suitable amplification primers. The hybridization probes may already be present during the amplification reaction or added subsequently.

After completion of the PCR-reaction, the temperature of the sample is constitutively increased, and fluorescence is detected as long as the hybridization probe was bound to the target DNA. At melting temperature, the hybridization probes are released from their target, and the fluorescent signal is decreasing immediately down to the background level. This decrease is monitored with an appropriate fluorescence versus temperature-time plot such that a first derivative value can be determined, at which the maximum of fluorescence decrease is observed.

However, in some cases and depending on the design of FRET hybridization probes or hybridization probes such as molecular beacons, the first derivatives of such temperature-time plots do not have the expected bell-shaped curves but comprise shoulders which cannot be explained by primary sequence analysis. The physico-chemical processes underlying the time course of melting DNA hybrids at present can not be predicted accurately by any mathematical model. Thus, in practice, a person skilled in the art needs to design and test several similar hybridization probes or pairs of FRET hybridization probes in order to identify and select a suitable pair which may generate melting curves having a more or less ideally bell shaped curve.

One possibility to overcome this problem is the introduction of artificial mismatches as it has been disclosed in WO 97/46711. However, introduction of mismatches only in some cases results in non ideally shaped melting curves, especially in case of multiplex analysis using several hybridization probes or several pairs of FRET hybridization probes in the same reaction vessel.

Thus there is a need in the art to provide oligonucleotides and especially FRET hybridization probes with an improved melting curve behavior.

BRIEF DESCRIPTION OF THE INVENTION

This problem is solved by providing oligonucleotides according to the invention.

More precisely, the present invention is directed to oligonucleotides comprising an axial molecular rod.

In a first embodiment, the molecular rod connects a first part and a second part of an oligonucleotide chain, characterized in that the molecular rod covalently connects the 3' end of a first nucleotide residue, said residue being the 3' terminal residue of said first part of said chain with the 5' end of a second nucleotide residue, said second nucleotide residue being the 5' terminal of said second part of said chain.

In a second embodiment, the molecular rod is covalently connected to the 5' position of the 5' terminal residue or to the 3' position of the 3' terminal residue. Preferably, the molecular rod is connected to the 5' or 3' end of the oligonucleotide via a phosphate moiety.

In another aspect, the present invention is directed to a composition comprising an oligonucleotide as disclosed above.

In a third aspect, the present invention is directed to a kit comprising an oligonucleotide as disclosed above.

In a further aspect, the present invention is directed to a phosphoramidite comprising a molecular rod.

An oligonucleotide containing a molecular rod according to the invention may for example be used as a primer for a primer extension reaction or a primer for a nucleic acid amplification reaction.

Alternatively, an oligonucleotide containing a molecular rod according to the invention may be used as a hybridization probe. In a specific embodiment, using a hybridization probe according to the invention, temperature dependence of hybridization is monitored, for example by means of performing a melting curve analysis.

An oligonucleotide comprising a molecular rod according to the invention may also become immobilized on a solid support. Preferentially, it is the molecular rod which connects the chain of nucleotide residues to the solid

The figure depicts the synthesis strategy for the generation of a phosphoramidite comprising a molecular rod, which according to the invention may be incorporated internally into an oligonucleotidy by conventional oligonucleotide synthesis chemistry. Details are explained in Example 1.

Figure 2:
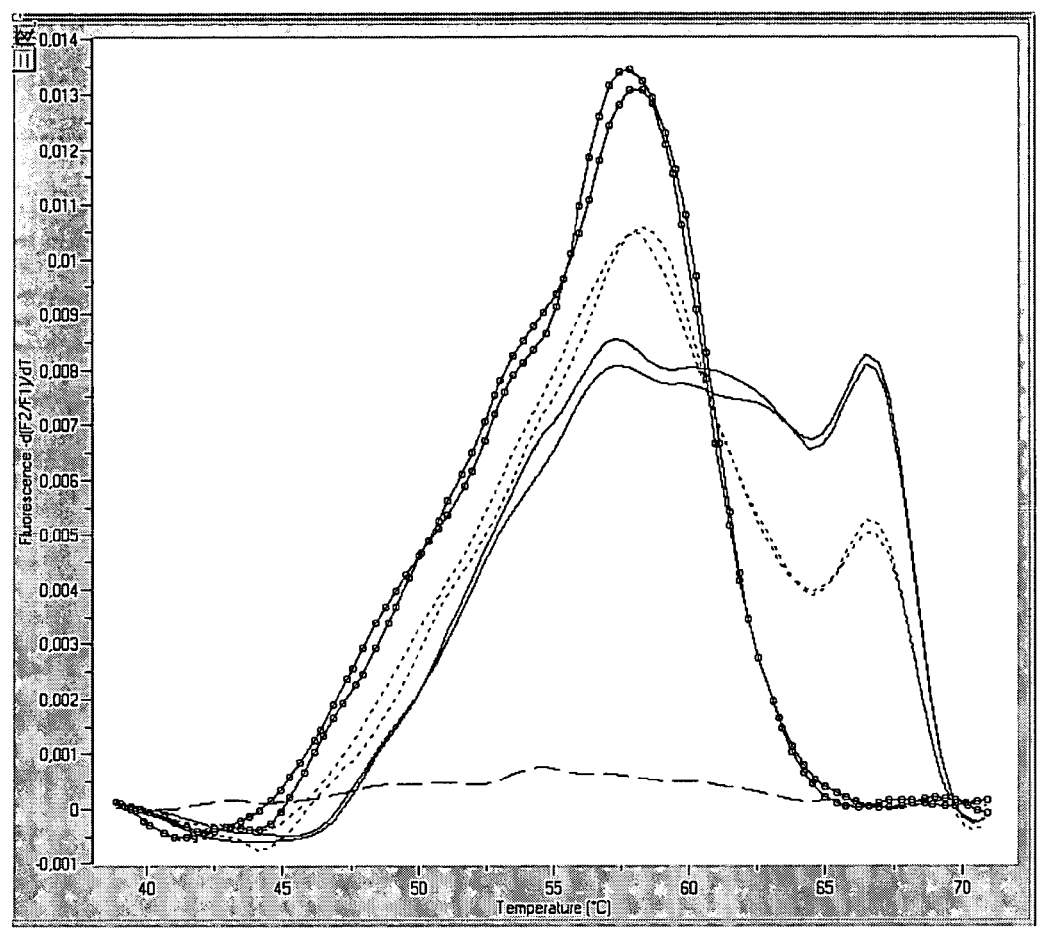

FIG. 2: Prothrombin Mutation Analysis 1 ng of prothrombin homozygous wildtype, heterozygous and homozygous mutant plasmid DNA was amplified. The hybridization probe, which spanned the mutation site (mutation probe), had 100% homology to the homozygous wildtype plasmid DNA.

Figure 3:
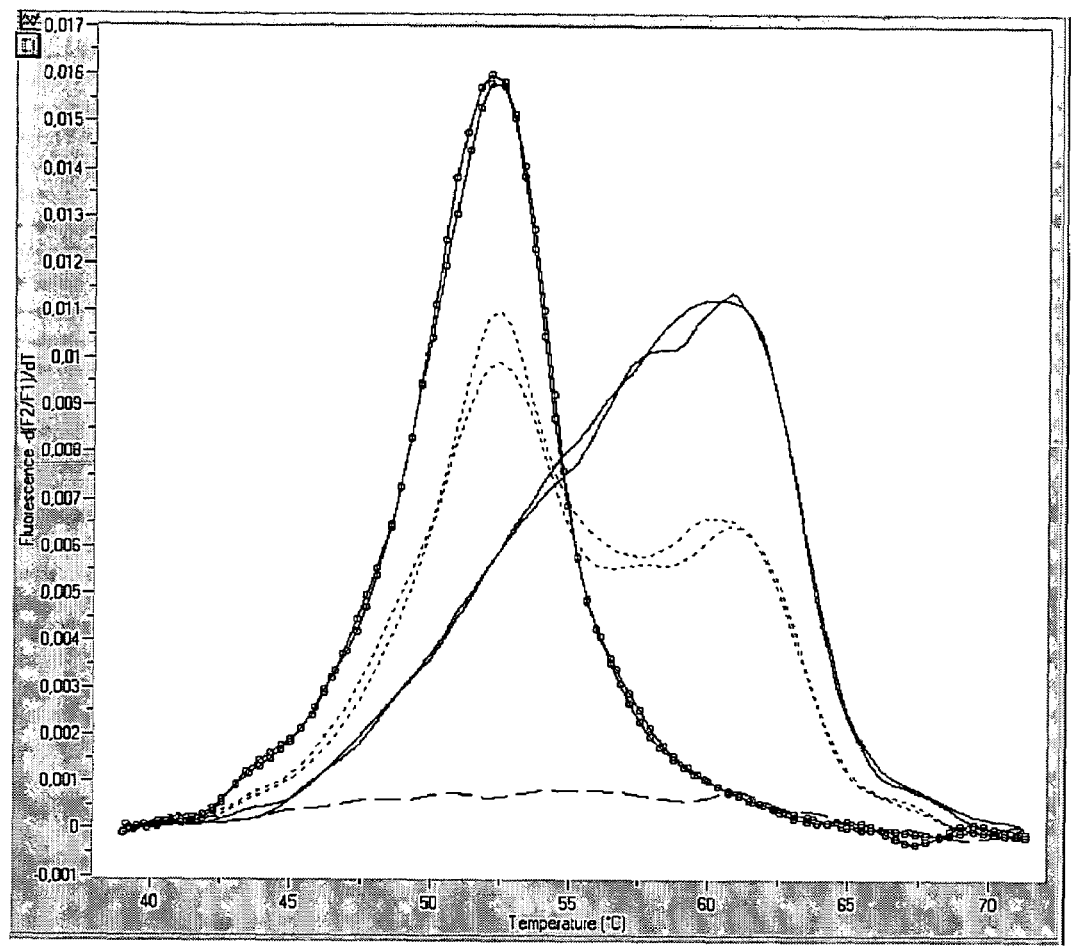

FIG. 3: Prothrombin Mutation Analysis with an Artificial Mismatch 1 ng of prothrombin homozygous wildtype, heterozygous and homozygous mutant plasmid DNA was amplified. The hybridization probe, which spanned the mutation site (mutation probe), carried an artificial mismatch.

Figure 4:
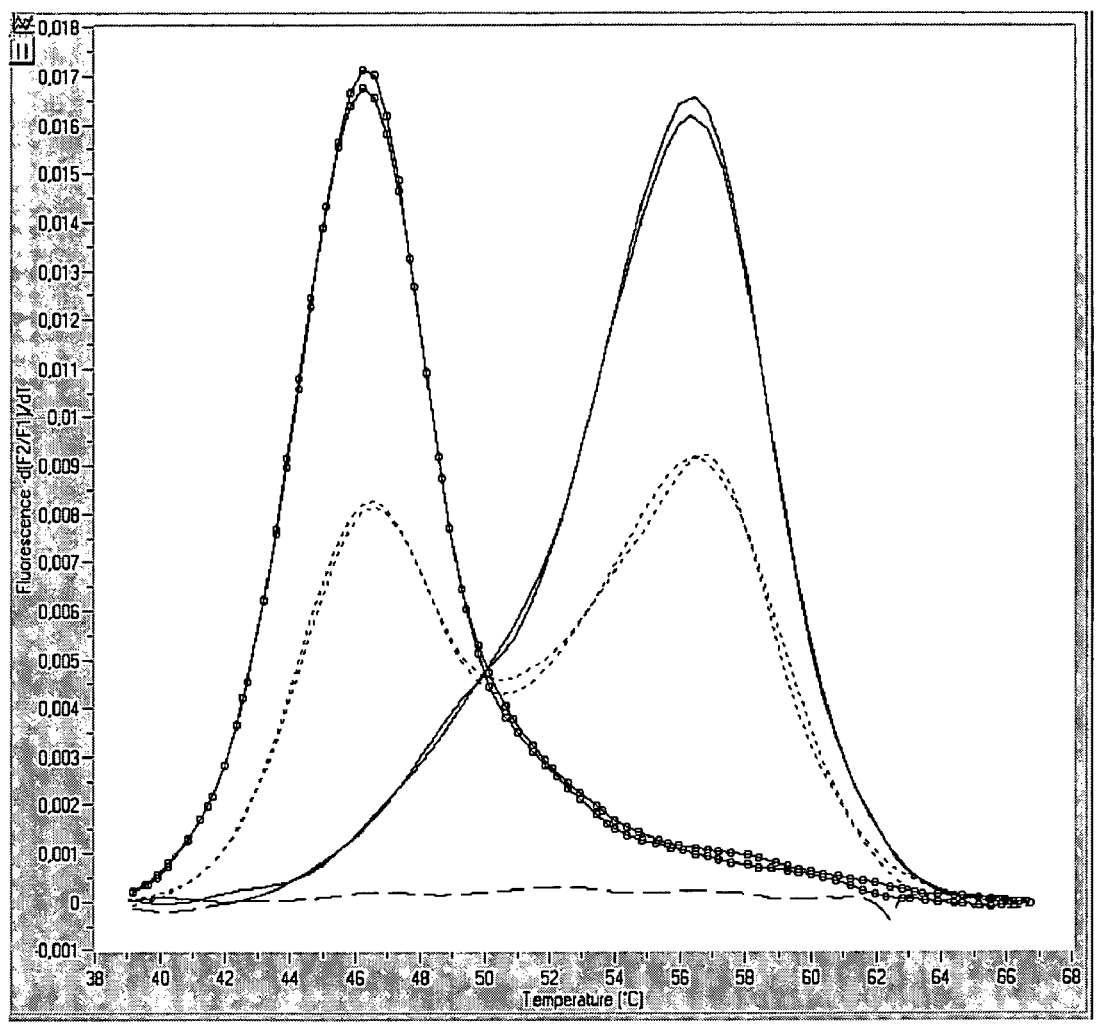

FIG. 4: Prothrombin Mutation Analysis with Inserted Phenylene Linker 1 ng of prothrombin homozygous wildtype, heterozygous and homozygous mutant plasmid DNA was amplified. The hybridization probe, which spanned the mutation site (mutation probe), carried an inserted phenylene linker FIG. 5: Prothrombin Mutation Analysis: TM Shift of the Melting Peaks Using Modified Mutation Probes 1 ng of prothrombin homozygous mutant plasmid DNA was amplified. Three different mutation probes were tested: one with 100% homology to the homozygous wildtype plasmid DNA, one with an artificial mismatch and one with an inserted phenylene linker.

Figure 6:
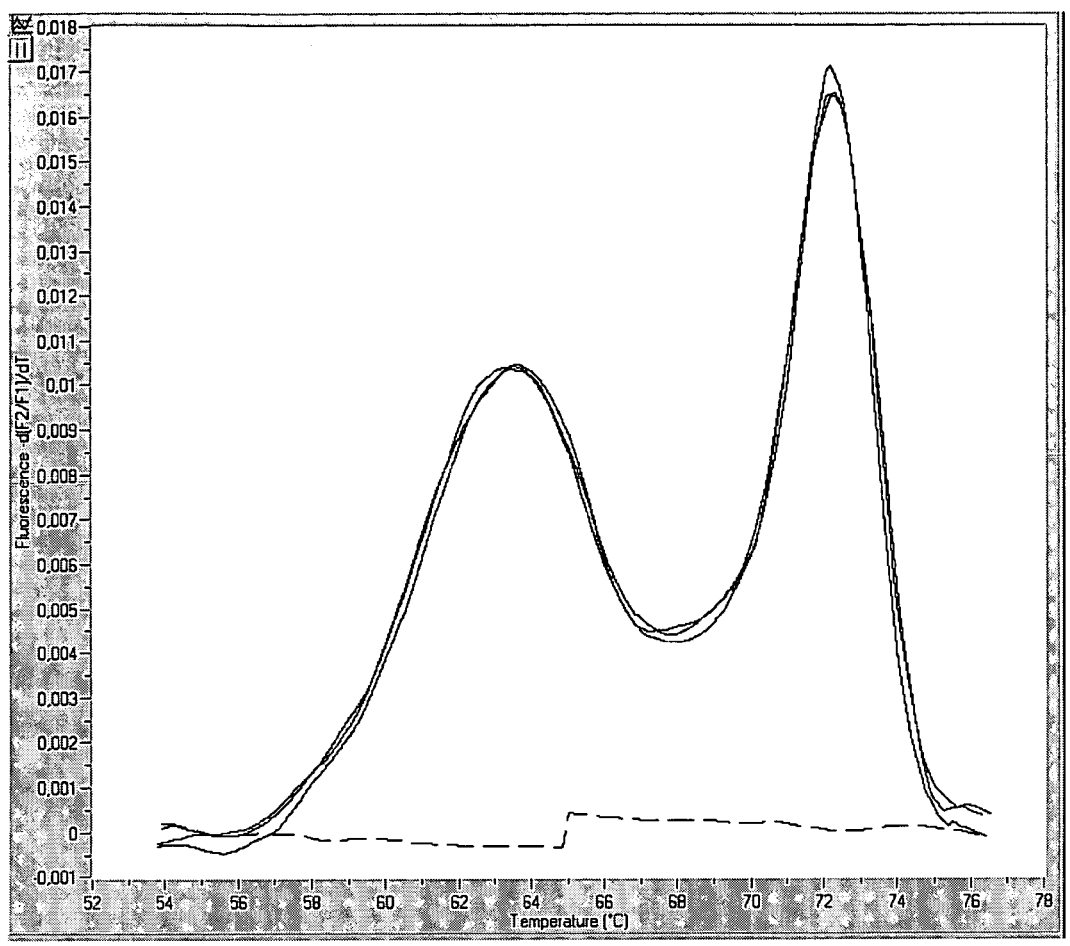

FIG. 6: EBV Detection with Perfect Matching Hybridization Probes 104 copies of EBV plasmid DNA were amplified. The LC Red 640 labeled hybridization probe, which determined the TM, showed 100% homology to the EBV plasmid DNA.

Figure 7:
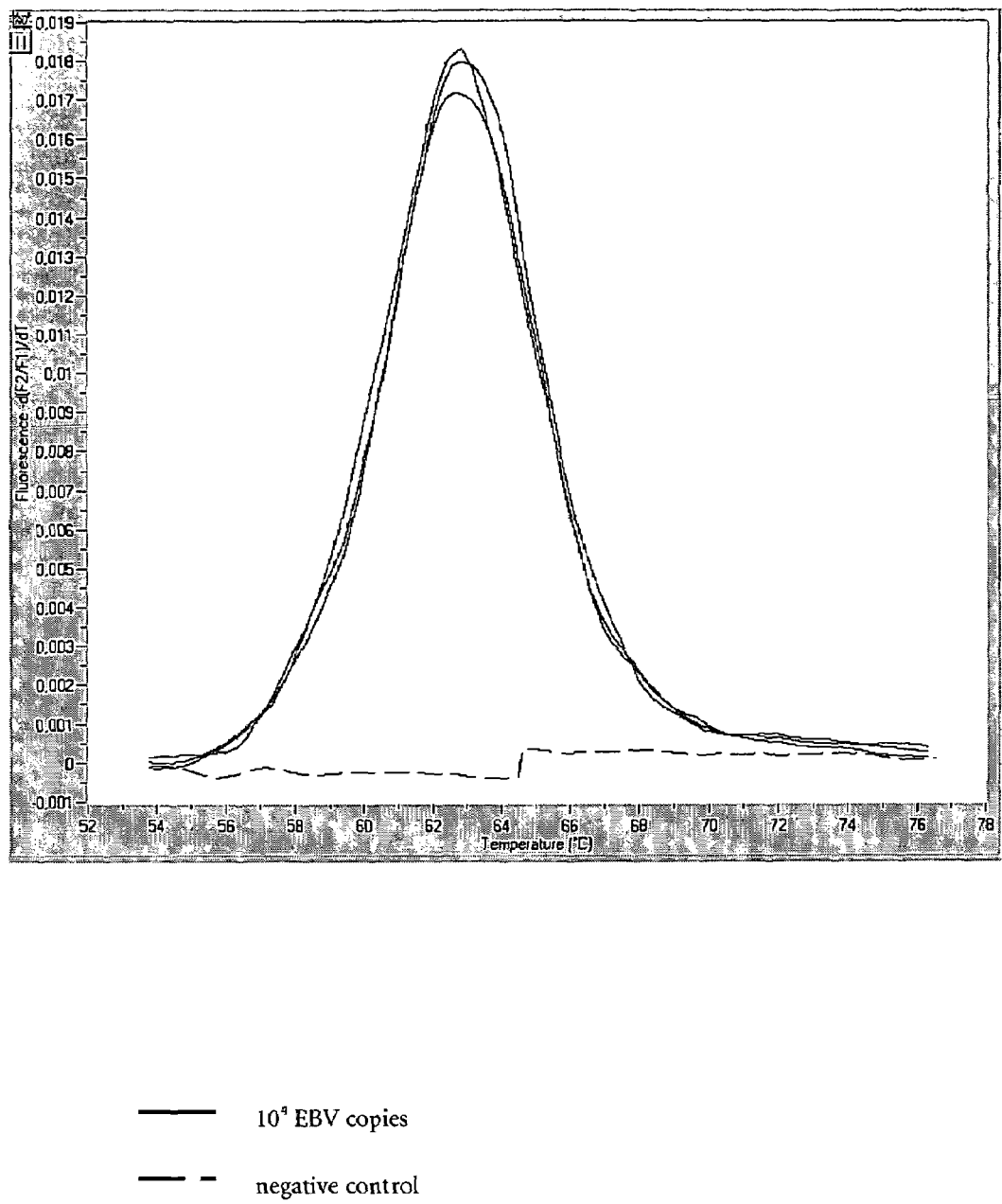

FIG. 7: EBV Detection with Hybridization Probes Carrying an Inserted Phenylene Linker 104 copies of EBV plasmid DNA were amplified. The LC Red 640 labeled hybridization probe, which determined the TM, carried an inserted phenylene linker.

DETAILED DESCRIPTION OF INVENTION

The present invention is directed to oligonucleotides comprising an axial molecular rod. A detailed review on molecular rods is given by Schwab et al., in Chem. Rev. 99 (1999) 1863-1933, the content of which is hereby incorporated in the disclosure of the present invention in its entirety by reference.

In the context of the present invention, axial molecular rods can be defined as linkers connecting two molecules (e.g. two parts of an oligonucleotide) in such a way that the two molecules, or two parts of the oligonucleotide are restricted in their motion relative to each other. In one embodiment, the relative positions of each of the carbon atoms that contribute to the rod structure are fixed. In other words, illustrative molecular rods are rigid structures which in themselves cannot be bent. As a consequence, the distance between the atoms of the two molecules which are covalently bound to the rod structure is fixed and cannot become altered. In another embodiment, two or more axial molecular rods are connected to each other and used as a linker connecting two molecules, e.g., two parts of an oligonucleotide. In one aspect of this latter embodiment, the two or more axial molecular rods are connected in a way that forms a rigid structure which in itself cannot be bent. In another aspect of this latter embodiment, the two or more axial molecular rods are connected in a way that there is some flexibility between some or all of the two or more axial molecular rods such that they may move relative to each other.

Within the scope of the present invention, any kind of molecular rod which is compatible with oligonucleotide synthesis protocols may be used. Preferably, rods used for the synthesis of oligonucleotides according to the invention are small simple chemical structures which are composed of only a few carbon atoms. Also preferred are those types of molecular rods which can be synthesized very cheaply and easily by conventional methods of organic chemistry starting from basic compounds which are preferably commercially available.

In a preferred embodiment, the rod is a singly linked axial molecular rod. By definition, singly linked axial molecular rods are linked by a single covalent bond to each of the two molecules connected by the rod. For example, the molecular rod is simply composed of two carbon atoms linked by an ethyne. Other examples for singly linked molecular rods not limiting the scope of the invention are bicyclopentane, bicyclclooctane, cubane, benzene, naphtalene, anthracene, pyrene, pyridine, or porphyrine. Molecules and especially oligonucleotides linked by a connecting singly axial molecular rod can be rotated relatively against each other, although the distance between the atoms of the two molecules which are covalently bound to the rod structure is fixed.

In a highly preferred embodiment the singly linked axial molecular rod comprises or consists of either an ethyne moiety or, alternatively, a phenylene moiety.

In another highly preferred embodiment, the singly linked axial molecular rod comprises or consists of a molecular structure as follows:

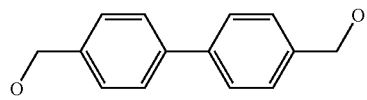

In an alternative embodiment, the rod is a doubly linked axial molecular rod. By definition, doubly linked axial molecular rods are linked by two covalent bonds to each of the two molecules connected by the rod. Examples for doubly linked axial molecular rods include ethene, cyclobutane, cyclohexane, and cyclohexadiene. Molecules and especially oligonucleotides linked by a connecting doubly axial molecular rod can not be rotated relatively against each other, in addition to the fact that the distance between the atoms of the two molecules which are covalently bound to the rod structure is fixed.

It is also within the scope of the present invention that the axial molecular rod of an oligonucleotide is composed from several modules, each of which is a molecular rod, such as polyethylene formed from two or more ethyne molecular rods. Therefore, depending on the number of modules which are used, the length of the axial molecular rod may be adjusted as required accordingly.

Synthesis of oligonucleotides comprising molecular rods may be performed according to conventional oligonucleotide synthesis chemistry.

In one embodiment, the molecular rod is covalently bound to the 3'-OH position of the 3' terminal residue or to the 3' position of the 3' terminal residue. For this embodiment, an axial molecular rod may be introduced at the 3' end of a chemically synthesized oligonucleotide using an appropriate CPG (controlled pore glass) comprising a trifunctional spacer. This can either be done by applying a CPG already carrying a molecular rod analogous to the compounds and methods disclosed in U.S. Pat. No. 5,290,925.

In another embodiment, the molecular rod is covalently bound to the 5'-position of the 5' terminal residue. For this other embodiment, an axial molecular rod may be linked to a nascent oligonucleotide chain by using an appropriate phosphoramidite. Optionally, an amino group at the free end of the rod can be introduced which may serve as a basis for subsequent conventional post labeling strategies.

The phosphoramidite chemistry method is well known by any person skilled in the art. A 3'-phosporous group of one nucleoside reacts with the 5'-hydroxyl moiety of another. The reaction proceeds from 3'- to 5'-, between each phosphoramidite with a 5'-dimethoxytrityl protected monomer delivered in solution and the growing, 3' reactive oligonucleotide bound to an inert substrate. In comparison to other methods, the inherent coupling yields are typically on the order of 98±0.5%, resulting in adducts that are easily purified. An important factor ensuring a high yield synthesis is the capping step—the acetylation of uncoupled bases at the 5'-hydroxyl moiety. The crude reaction mixture collected at the conclusion of each synthesis consists of the desired adduct, along with small quantities of side products. These deletion sequences range in size from one base to n−1 bases—where n is the number of bases in the desired product. Deletion sequences, which formed due to failed couplings, must be chemically capped prior to subsequent base additions. Otherwise these failed sequences would compete with the full length adduct for phosphoramidites. Also, the separation of the (n−1)-mer from the desired product is much more challenging than the separation of other truncated sequences of shorter length.

Nascent oligonucleotides have the 5'-hydroxyl positions protected by dimethoxytrityl (DMT) groups, which have to be removed after each synthesis cycle in order to generate a reactive 5' OH group of the nascent oligonucleotide chain. For product oligonucleotides, the DMT group can be removed during synthesis (TRITYL OFF) or left on (TRITYL ON) if reverse phase HPLC is the purification method of choice. A free 3'-hydroxyl moiety is created when the synthesized oligonucleotide is cleaved from the support, so no further deprotection is required.

The inventors of the present invention surprisingly discovered that hybridization probes comprising an internal molecular rod possess an altered and more predictable behavior in melting curve analysis experiments. Therefore, in one important embodiment of the present invention, the molecular rod connects a first part and a second part of an oligonucleotide chain, characterized in that the molecular rod covalently connects the 3' end of a first nucleotide residue, said residue being the 3' terminal residue of said first part of said chain with the 5' end of a second nucleotide residue, said second nucleotide residue being the 5' terminal of said second part of said chain.

There exists an easy possibility for generating oligonucleotides comprising an internal axial molecular rod. An appropriate phosphoramidite comprising an axial molecular rod may be introduced carrying an appropriately protected hydroxyl group, which during the next synthesis cycle may become deprotected such that it can react with another deoxynuclotide-phosphoramidite.

Figure 1:
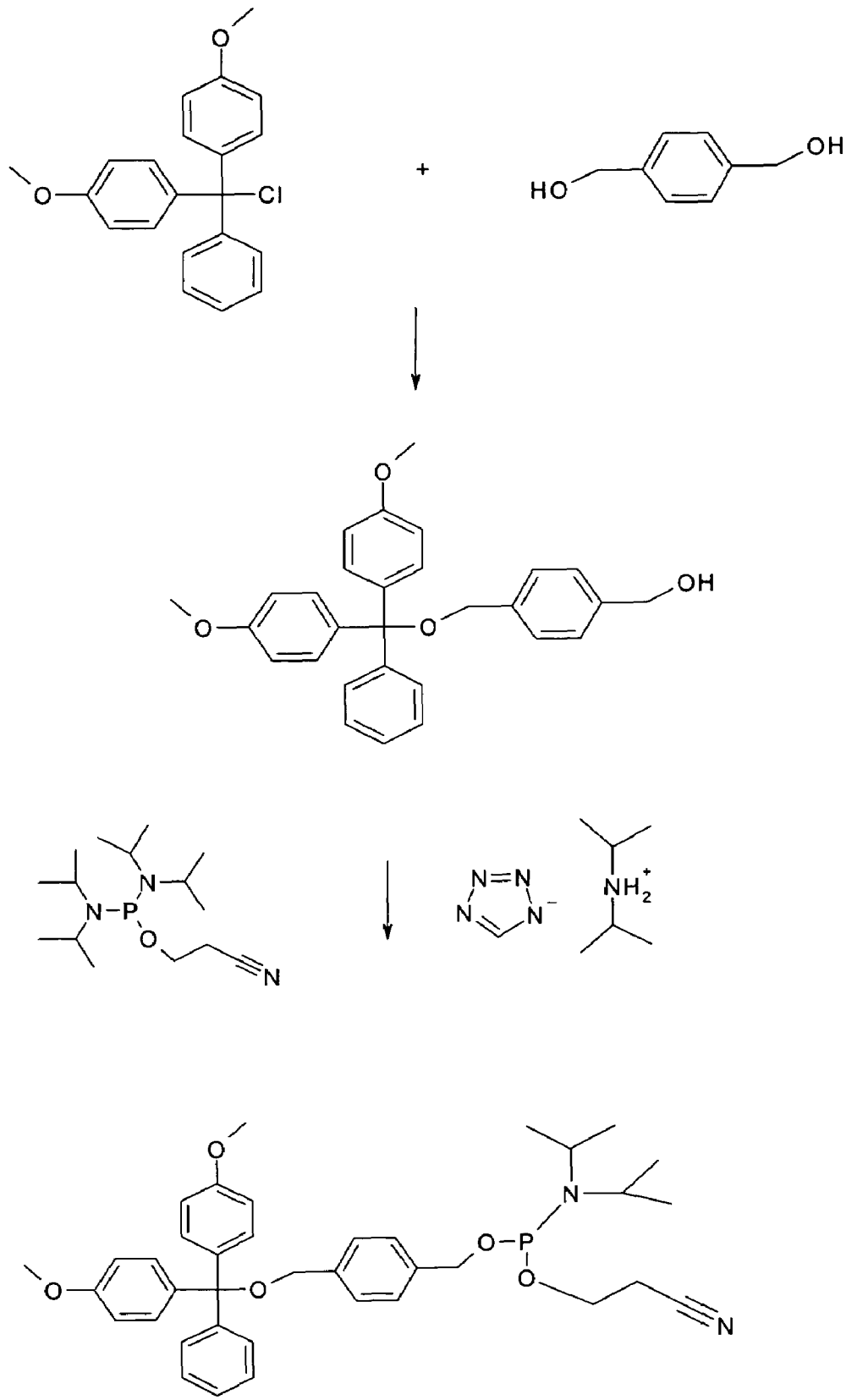
FIG. 1: Synthesis of a Phosphoramidite Comprising a Molecular Rod

An example for the synthesis of a phenylene phosphoramidite is given in FIG. 1 and Example 1. Other molecular rod phosphoramidites can be synthesized correspondingly, starting from rod scaffolds comprising, for example, two hydroxyl groups as reactive groups.

In another embodiment, several rod-carrying phosphoramidites may be coupled to the nascent oligonucleotide chain one after another in order to generate an oligonuceotide comprising an internal rod of appropriate length.

In another aspect, the present invention is directed to compositions comprising at least one oligonucleotide with axial molecular rods as disclosed above.

In still another aspect, the present invention is directed to a kit comprising an oligonucleotide as disclosed above.

In general, oligonucleotides comprising axial molecular rods according to the invention may be used for a variety of applications, for example as a primer for a primer extension reaction, as a primer for a nucleic acid amplification reaction, or as a hybridization probe.

In one embodiment, axial molecular rods may serve as linkers of labeled oligonucleotides between the oligonucleotide chain and the labeling entity. As a consequence, the rigid structure of the rod results in prevention of a partial vicinity between the labeling entity and the oligonucleotide chain. In case the label is a fluorescent entity, such an avoidance is highly advantageous, since undesired quenching effect due to an uncontrollable interaction between G residues and the fluorescent entity are avoided.

In another important embodiment, oligonucleotides containing internal axial molecular rods according to the invention are used as hybridization probes. The axial molecular rods may be an integral part of any kind of hybridization probes such as TAQMAN probes, Molecular Beacons or may be in integral part of one or both members of a pair of FRET hybridization probes. Those hybridization probes according to the invention may be used for hybridization on blots, microtiter plates, microarrays, and, in particular for real time PCR.

In a specific embodiment, using a hybridization probe or a pair of FRET hybridization probes according to the invention, temperature dependence of hybridization is monitored, for example by means of performing a melting curve analysis.

Real time PCR melting curve analysis is usually performed after completion of the PCR-reaction. After an initial denaturation and cooling step, the temperature of the amplicon is constitutively increased, and fluorescence is detectable as long as the hybridization probe is bound to the target DNA. In case of the FRET hybridization probe formate, both probes need to stay hybridized to the target nucleic acid in order to generate a fluorescent signal. At melting temperature, the hybridization probes (in case of the FRET format: at least one member of said pair of hybridization probes) are released from their target, and the fluorescent signal is decreasing immediately down to the background level.

This decrease is monitored with an appropriate fluorescence versus temperature-time plot such that a first derivative value can be determined, at which the maximum of fluorescence decrease is observed. As it will be demonstrated by the examples below, oligonucleotides containing internal axial molecular rods according to the invention will be highly advantageous for this particular embodiment.

Due to the rigid nature of the axial molecular rod, the melting characteristic of an oligonucleotide can be altered substantially and thus adjusted to the required conditions.

First, introduction of an internal molecular rod may result in a moderate shift in the melting temperature™ of the oligonucleotide which is usually a moderate temperature decrease. Such a decrease may be advantageous especially for multiplex melting curve approaches, where multiple Tms have to be analyzed and discriminated from each other.

Second, introduction an internal molecular rod usually results in an increase in the difference of melting temperatures detectable when compared hybridization events with and without base pairing mismatches. Therefore, oligonucleotides according to the invention significantly improve allelic discrimination and analysis of single nucleotide polymorphism analysis in real time PCR as well as in embodiments using solid supports.

Third, introduction an internal molecular rod in all cases investigated so far results in sharp, slender and optimally bell shaped melting peaks when first derivative temperature versus time plots are produced. This could be explained by the rigid nature of the axial molecular rods, which results in a situation where the respective hybridization probe is either still completely hybridized to the target DNA, or completely free in its single stranded form in the reaction solution. In other words: partially hybridization intermediates resulting in non bell shaped melting curves with shoulders are avoided.

Fourth, usage of probes containing internal axial molecular rods results in many cases in an improvement of assay specificity.

In a final aspect, oligonucleotides comprising an axial molecular rod according to the invention may also become immobilized on a solid support, for example a nucleic acid microarray. Preferentially, it is the molecular rod which connects the chain of nucleotide residues to the solid support. Such an application is highly advantageous, because the rigid structure of the rods leads to a limited, defined and controllable spatial separation between the oligonucleotide itself and the solid support. As a consequence, a putative sterical hindrance of hybridization to the immobilized oligonucleotides caused by the vicinity to the solid support is avoided.

Since for nucleic acid array applications it is particularity important to achieve an optimized match/mismatch discrimination, introduction an internal molecular rod according to the invention is highly advantageous, because it results in an increase in the difference of melting temperatures detectable when hybridization events with and without base pairing mismatches are compared.

The appropriate mode of coupling of the molecular rod onto the solid support depends on the type of solid support which actually shall be used. For example, amino groups of the rod may react with epoxy-groups on the surface such as glass or plastic. Alternatively, alkoxy-silanated rods may be coupled to glass surfaces. For surfaces carrying reactive C—OH groups, linkage may be obtained using conventional phosphoramidate cheimstry.

In order to control the density of oligonucleotides immobilized by in situ synthesis onto solid support, the solid support is in a first step reacted with a mixed solution of axial molecular rods exendable by oligonucleotides synthesis and non extendable axial molecular rods. Density can then be adjusted by amending the concentration of non extendable rod compounds.

The following examples, references, sequence listing and figures are provided to aid the understanding of the present invention, the true scope of which is set forth in the appended claims. It is understood that modifications can be made in the procedures set forth without departing from the spirit of the invention.

EXAMPLES

Example 1

Synthesis of an Oligonucleotide Comprising a Molecular Rod

As an example for the synthesis of an oligonucleotide according to the invention, an oligonucleotide according to the invention carrying an internal rod was synthesized according to the strategy depicted in FIG. 1 as follows:

A) 4-(p,p'-Dimethoxytrityl-methyloxy)benzyl Alcohol

Within 1 h a solution of 51.5 g Dimethoxytritylchlorid in 300 ml dry pyridine was dropped at room temperature to a solution of 20 g of 1,4 bis hydroxymethylbenzol in 100 ml dry pyridine. After stirring overnight the solvent was evaporated using a rotary evaporator. The residue was dissolved in 800 ml acetic acid ethyl ester and was washed with once with 400 ml and than with two times 200 ml water. The organic phase was separated and dried with sodium sulfate. After filtration the solvent was removed by using a rotary evaporator.

Purification was performed by column chromatography on silica gel. Therefore 10 grams of the crude product were dissolved in a Toluol/Acetic Acid Ethyl ester/Methanol 4:1:1 mixture containing 0.1% Triethylamin. The solution was applied on a 40 cm/d=6.9 cm column filled with silica gel 60 (0.063-0.200 mm). The product was eluated with a Toluol/Acetic Acid Ethyl ester/Methanol 4:1:1 mixture containing 0.1% Triethylamin.

TLC: Toluol/Acetic Acid Ethyl ester/Methanol 4:1:1 mixture containing 0.1% Triethylamin Rf: 0.56

B) Diisopropyl-phosphoramidous acid 4-[bis-(4-methoxy-phenyl)-phenyl-methoxy]-benzyl ester 2-cyano-ethyl Ester At room temperature under argon 0.78 gram diisopropylammonium tetrazolid were added to a solution of 2 grams of 1-(O-Dimethoxytrityl-hydroxymethyl) 4-hydroxymethylbenzol in dry 15 ml Methylenehloride. A solution of 1.37 g of 2-cyanoethyl-tetra isopropyl-phosphordiamidit in 10 ml dry Methylenehloride was added drop wise within 30 min. After stirring at room temperature for 2h the suspension was filtrated. From the filtrate the solvent was removed by using a rotary evaporator. The residue was dissolved in 50 ml acetic acid ethyl ester and washed two times with 10 ml 5% aqueous sodium hydrogencarbonat solution. The organic phase was separated and dried with sodium sulfate. After filtration the solvent was removed by using a rotary evaporator.

Purification was performed by column chromatography on silica gel. Therefore the crude product was dissolved in an Acetic Acid Ethylester/Hexane 1:1 mixture containing 0.1% Triethylamin. The solution was applied on a 1=32 cm/d=4.5 cm column filled with silica gel 60 (0.063-0.200 mm). The product was eluated with an Acetic Acid Ethyl ester/Hexane 1:1 mixture containing 0.1% Triethylamin:

TLC: Acetic Acid Ethyl ester/Hexane 1:1 mixture containing 0.1% Triethylamin Rf: 0.80

NMR 1H(300 MHz): 1.21 t[12H], 2.76 t[2H], 3.7 m[2H], 3.78 s[6H], 3.88 m[2H], 4.16 s[2H], 4.75 m[2H], 6.91 d[4] 7.23-7.67 m,s [13] NMR 31P(300 MHz): 149.19

The resulting phosphoramidate was incorporated into oligonucleotides by conventional oligonucleotide synthesis using phosphoramidate chemistry. A molecular rod in the oligonucleotide as synthesized above will be termed "phenylene linker" in the examples which follow.

Example 2

Real Time Mutation Analysis of Prothrombin Plasmid DNA

To demonstrate the validity of the invention, genotyping of the prothrombin (G20210A) point mutation by using hybridization probes was chosen as test system.

Partial fragments of wildtype and mutant prothrombin sequence were cloned into separate pCRTM 2.1 plasmid vectors (Invitrogen). Concentration of plasmid DNA was estimated by spectrophotometry. Prothrombin plasmid DNA dilutions and mixtures of wildtype and mutant plasmid to get heterozygous DNA were prepared by using a diluent consisting of MS2 RNA (10 ng/µl) in 10 mM Tris-HCl, pH 8.3.

PCR was conducted on a LIGHTCYCLER instrument (Roche Molecular Biochemicals). A typical PCR assay consisted of 2 µl DNA, 1× Detection Mix, 1× Reaction buffer, 4 mM magnesium chloride and 1.6 units of Taq polymerase (all from Roche Diagnostics, Mannheim, Germany) adjusted with water to a 20 µl volume in one reaction capillary.

For mutation analysis, the reaction buffer and the unmodified Taq polymerase from the LIGHTCYCLER-DNA Master Hybridisation Probes Kit (Roche Molecular Biochemical, Cat. No. 2 015 102) were used.

The 10× Detection Mixes for prothrombin consisted of 5 µM of each primer (forward and reverse), 2 µM of mutation probe (Fluorescein-labeled), 4 µM of anchor probe (LC Red 640-labeled), 0.05% Brij-35 in 10 mM Tris-HCl, pH 8.3 buffer.

The following primer and hybridization probe sequences were used:

```
Prothrombin forward primer:
5'CCAATCCCGTGAAAGAATTAT-3'           (SEQ ID NO: 1)

Prothrombin reverse primer:
5'-AGGTGGTGGATTCTTAAGTC-3'           (SEQ ID NO: 2)

Prothrombin probe 1:
                                     (SEQ ID NO: 3)
5'-LCRed640-CACTTTTATTGGGAACCATAGTTTTAGAAACACAAphosphate-3'

Prothrombin probe 2:
                                     (SEQ ID NO: 4)
5'-GCATTGAGGCTCGCTGAGAG-fluorescein-3'

Prothrombin probe 3:
                                     (SEQ ID NO: 5)
5'-GCATTGTGGCTCGCTGAGAG-fluorescein-3'

Prothrombin probe 4:
                                     (SEQ ID NO: 6)
5'-GCATTGxGGCTCGCTGAGAG-fluorescein-3' x = phenylene linker
```

Regular PCR cycling conditions consisted of an initial 95° C. incubation for 30 seconds followed by 45 cycles of 95° C. for 0 seconds, 55° C. for 10 seconds and 72° C. for 5 seconds and was concluded with 40° C. for 30 seconds.

Melting Temperatures for each reaction were determined by the LIGHTCYCLER Analysis software using the polynomial calculation method with background subtraction.

Example 3

Genotyping of the Prothrombin (G20210A) Point Mutation is not Possible with the Perfect Matching Mutation Probe Real time PCR of 1 ng wildtype, heterozygous and mutant prothrombin DNA was performed in a setup according to Example 1. Results are shown in FIG. 2. As can be seen, after performing a melting curve analysis with a perfect matching mutation probe it is not possible to determine the prothrombin genotype exactly, since the homozygous wildtype and the heterozygous genotype could not be differentiated exactly.

Example 4

Using a Mutation Probe with an Artificial Mismatch Genotyping of the Prothrombin (G20210A) Point Mutation is Possible, But not Perfect Real time PCR of 1 ng wildtype, heterozygous and mutant prothrombin DNA was performed in a setup according to Example 1. Results are shown in FIG. 3. As can be seen, correct determination of the prothrombin genotype is principally possible using the mutation probe with an artifical mismatch, but the wildtype melting peak is still very broad and shows a distinct shoulder. Additionally, the minimum between the two melting peaks of the heterozygous samples has a high signal level, so there is no big difference between the minimum between the peaks and the maximum of the wildtype melting peak.

Example 5

Perfect Genotyping of the Prothrombin (G20210A) Point Mutation can be Performed Using the Mutation Probe with an Inserted Phenylene Linker Real time PCR of 1 ng wildtype, heterozygous and mutant prothrombin DNA was performed in a setup according to Example 1. Results are shown in FIG. 4. As can be seen, the prothrombin genotype can be determined perfectly using the mutation probe with an inserted phenylene linker. All melting peaks are very sharp and without any shoulders.

Example 6

Figure 5:
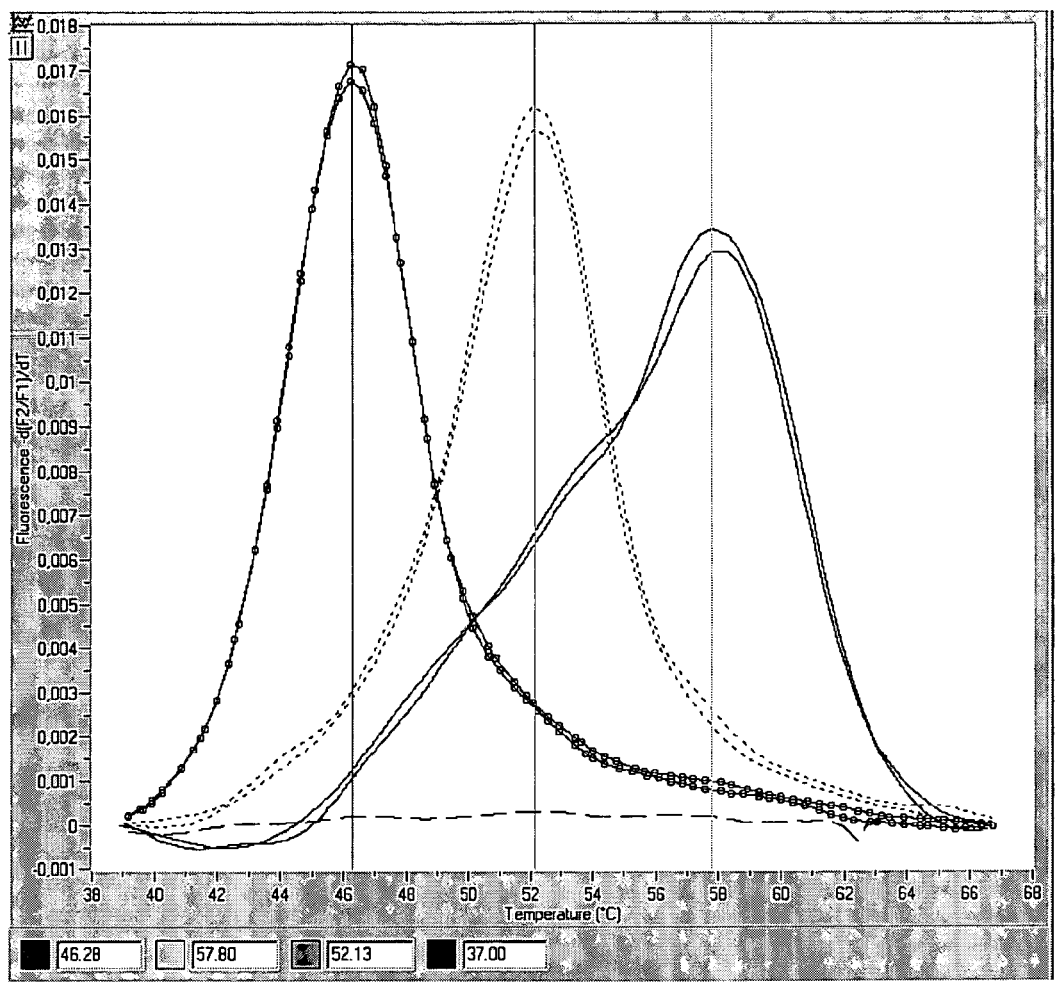

Shift of the Melting Temperature of the Prothrombin Mutation Melting Peak Using Different Mutation Probes Real time PCR of 1 ng mutant prothrombin DNA was performed in a setup according to Example 1. Results are shown in FIG. 5. As can be seen, the melting temperature of the prothrombin mutation melting peak shifts dependent on the used mutation probe. The table below shows the different melting temperatures.

| | $T_M$ (° C.) | $\Delta T_M$ (° C.) |
|---|---|---|
| Mutation probe with perfect match | 57.80 | 5.67 |
| Mutation probe with an artifical mismatch | 52.13 | 5.85 |
| Mutation probe with inserted Hauberlinker | 46.28 | |

Example 7

Real Time PCR of EBV Plasmid DNA

To demonstrate the validity of the invention, Epstein-Barr virus, frequently referred to EBV, a member of the herpes virus family and one of the most common human viruses, was chosen as second test system.

A partial fragment of EBV was cloned into the pT3T7 plasmid vector (Roche Molecular Biochemicals). Copy numbers of plasmid DNA were estimated by spectrophotometry with the assumption that 1 mole is equivalent to 6×1023 copies. EBV plasmid DNA dilutions were prepared by using a diluent consisting of MS2 RNA (10 ng/μl) in 10 mM Tris-HCl, pH 8.3.

PCR was conducted on a LIGHTCYCLER instrument (Roche Molecular Biochemicals). A typical PCR assay consisted of 5 μl DNA, 1× Detection Mix, 1× Reaction buffer, 3.5 mM magnesium chloride and 1.6 units of modified Taq polymerase (all from Roche Diagnostics, Mannheim, Germany) adjusted with water to a 20 μl volume in one reaction capillary.

For PCR, the reaction buffer and the modified Taq polymerase from the LIGHTCYCLER-Fast Start DNA Master hybridization probes Kit (Roche Molecular Biochemical, Cat. No. 3 003 248) were used.

The 10× Detection Mixes for EBV consisted of 5 μM of each primer (forward and reverse), 2 μM of each hybridization probe (Fluorescein and LC Red 640 labeled), 0.05% Brij-35 in 10 mM Tris-HCl, pH 8.3 buffer.

The following primer and hybridization probes sequences were used:

```
EBV forward primer:
5'-ATGAGGAACGTGAATCTAATGA-3'      (SEQ ID NO: 7)

EBV reverse primer:
5'-TACAGATAGATGGCACTCTTACCTT-3'   (SEQ ID NO: 8)

EBV probe 1:
                                  (SEQ ID NO: 9)
5'-GGGATTGCAACACGACGGGAATGACG-fluorescein-3'

EBV probe 2:
                                  (SEQ ID NO: 10)
5'-LCRed640-GCTCCCTCCCCCTCCCTACTCTC-phosphate-3'

EBV probe 3:
                                  (SEQ ID NO: 11)
5'-LCRed640-GCTCCCTCCCCCTCxCTACTCTC-phosphate-3' x = phenylene linker
```

Regular PCR cycling conditions consisted of an initial 95° C. incubation for 10 minutes followed by 45 cycles of 95° C. for 10 seconds, 55° C. for 15 seconds and 72° C. for 15 seconds and was concluded with 40° C. for 30 seconds.

Melting Temperatures for each reaction were determined by the LIGHTCYCLER Analysis software using the polynomial calculation method with background subtraction.

Example 8

With Perfect Matching Hybridization Probes a Double Melting Peak is Generated Real time PCR of 104 copies EBV was performed in a setup according to Example 6. Results are shown in FIG. 6. As can be seen, performing a melting curve analysis with perfect matching hybridization probes a double peak and not the expected single melting peak was generated.

Example 9

Using the Hybridization Probe with an Inserted Phenylene Linker a Single Melting Peak is Generated Real time PCR of 104 copies EBV was performed in a setup according to Example 6. Results are shown in FIG. 6. As can be seen, if the hybridization probe, which determined the TM, carried an inserted phenylene linker, the expected single melting peak was generated after performing a melting curve analysis.

What is claimed is:

1. An oligonucleotide comprising an internal axial molecular rod, wherein the molecular rod is a singly-linking axial molecular rod selected from the group consisting of an ethyne, a bicyclopentane, a bicyclooctane, acubane, a benzene, a napihalene, a pyrene, a pyridine, a phenylenc, a prophyrin, and combinations thereof, or a doubly-linking axial molecular rod selected from the group consisting of an ethylene, a cyclobutane, a cyclohexane, a cyclohexadiene, and combinations thereof, wherein the molecular rod is a rigid structure which does not bend and which covalently bonds two internal molecules of the oligonucleotide, one at each axial end of the rod, so that a distance between atoms of the two molecules covalently bound to the rod is fixed.

2. An oligonucleotide comprising an axial molecular rod covalently bonded to a terminal residue of the oligonucleotide, wherein the molecular rod is a singly-linking axial molecular rod selected from the group consisting of an ethyne, a bicyclopentane, a bicyclooctane, a cubane, a benzene, a napthalene, a pyrene, a pyridine, a phenylene, a prophyrin, and combinations thereof, or a doubly-linking axial molecular rod selected from the group consisting of an ethylene, a cyclobutane, a cyclohexane, a cyclohexadiene, and combinations thereof.

3. The oligonucleotide of claim 2 wherein the axial molecular rod is covalently bonded to the 3' position of the 3' terminal residue of the oligonucleotide.

4. The oligonucleotide of claim 2 wherein the axial molecular rod is covalently bonded to the 5' position of the 5' terminal residue of the oligonucleotide.

5. An oligonucleotide intermediate comprising a phosphoramidite wherein the phosphoramidite comprises an axial molecular rod.

6. The oligonucleotide intermediate of claim 5 wherein the molecular rod is a singly-linked axial molecular rod.

7. The oligonucleotide intermediate of claim 6 wherein the molecular rod comprises a chemical group selected from the group consisting of an ethyne, a bicyclopentane, a bicyclooctane, a cubane, a benzene, a napthalene, a pyrene, a pyridine, a phenylene, a porphyrin, and combinations thereof.

8. A kit comprising an oligonucleotide wherein the oligonucleotide comprises an internal axial molecular rod, wherein the molecular rod is a rigid structure which does not bend and which covalently bonds two internal molecules of the oligonucleotide, one at each axial end of the rod, so that a distance between atoms of the two molecules covalently bound to the rod is fixed.

9. The kit of claim 8 wherein the axial incilecular rod is a singly-linked axial molecular rod.

10. The kit of claim 9 wherein the molecular rod comprises a chemical group selected from the group consisting of an ethyne, a bicyclopentane, a bicyclooctane, a cubane, a benzene, a napthalene, a pyrene, a pyridine, a phenylene, a porphyrin, and combinations thereof.

11. The kit of claim 8 wherein the molecular rod is a doubly-linked axial molecular rod.

12. The kit of claim 11 wherein the molecular rod comprises a chemical group selected from the group consisting of an ethyne, a cyclobutane, a cyclohexane, a cyclohexadiene, and combinations thereof.

13. A kit comprising an oligonucleotide according to claim 2.

14. The kit of claim 13 wherein the axial molecular rod is covalently bonded to the 5' position of the 5' terminal residue of the oligonucleotide.

15. The, kit of claim 13 wherein the axial molecular rod is covalently bonded to the 3' position of the 3' terminal residue of the oligonucleotide.

16. The kit of claim 15 wherein the molecularrod is a singly-linked axial molecular rod.

17. The kit of claim 16 wherein the molecular rod comprises a chemical group selected from the group consisting of an ethyne, a bicyclopentane, a bicyclooctane, a cubane, a benzene, a napthalene, a pyrene, a pyridine, a phenylene, a porphyrin, and combinations thereof.

* * * * *